(12) United States Patent
Medoff et al.

(10) Patent No.: US 9,359,620 B2
(45) Date of Patent: Jun. 7, 2016

(54) PROCESSING BIOMASS

(71) Applicant: XYLECO, INC., Woburn, MA (US)

(72) Inventors: Marshall Medoff, Brookline, MA (US); Thomas Craig Masterman, Rockport, MA (US); Seul-a Bae, Arlington, MA (US); Kelly Wallick, Somerville, MA (US)

(73) Assignee: Xyleco, Inc., Woburn, MA (US)

( * ) Notice: Subject to any disclaimer, the term of this patent is extended or adjusted under 35 U.S.C. 154(b) by 0 days.

(21) Appl. No.: 14/483,766

(22) Filed: Sep. 11, 2014

(65) Prior Publication Data

US 2014/0377818 A1    Dec. 25, 2014

Related U.S. Application Data

(63) Continuation of application No. 13/184,138, filed on Jul. 15, 2011, now Pat. No. 8,852,901.

(60) Provisional application No. 61/365,493, filed on Jul. 19, 2010.

(51) Int. Cl.

| | |
|---|---|
| *C12P 7/64* | (2006.01) |
| *C12P 7/56* | (2006.01) |
| *C12P 7/42* | (2006.01) |
| *C12P 7/54* | (2006.01) |
| *C12P 7/10* | (2006.01) |
| *C12P 7/46* | (2006.01) |
| *C12P 7/40* | (2006.01) |
| *C12P 7/14* | (2006.01) |
| *C12P 5/02* | (2006.01) |

(52) U.S. Cl.
CPC ... *C12P 7/14* (2013.01); *C12P 5/02* (2013.01); *C12P 5/023* (2013.01); *C12P 5/026* (2013.01); *C12P 7/10* (2013.01); *C12P 7/40* (2013.01); *C12P 7/42* (2013.01); *C12P 7/46* (2013.01); *C12P 7/54* (2013.01); *C12P 7/56* (2013.01); *C12P 7/6409* (2013.01); *C12P 2201/00* (2013.01); *C12P 2203/00* (2013.01); *Y02E 50/16* (2013.01); *Y02E 50/343* (2013.01)

(58) Field of Classification Search
None
See application file for complete search history.

(56) References Cited

U.S. PATENT DOCUMENTS

| | | | | |
|---|---|---|---|---|
| 6,444,437 | B1 * | 9/2002 | Sporleder et al. | 435/42 |
| 7,931,784 | B2 * | 4/2011 | Medoff | 204/157.63 |
| 8,212,087 | B2 * | 7/2012 | Medoff | 568/878 |

(Continued)

FOREIGN PATENT DOCUMENTS

WO    0160752    8/2001

OTHER PUBLICATIONS

Hall et al., Jul. 9, 2009; Nutrition and Feeding of the Cow-Calf Herd: Digestive System of the Cow, Virginia Cooperative Extension, Publication 400-010.*

(Continued)

*Primary Examiner* — Karen Cochrane Carlson
*Assistant Examiner* — Jennifer M. H. Tichy
(74) *Attorney, Agent, or Firm* — Wilmer Cutler Pickering Hale and Dorr LLP (57) ABSTRACT

Biomass (e.g., plant biomass, animal biomass, and municipal waste biomass) is processed to produce useful intermediates and products, such as energy, fuels, foods or materials. For example, methods are described that can use feedstock materials, such as cellulosic and/or lignocellulosic materials, to produce an intermediate or product, e.g., by fermentation.

25 Claims, 3 Drawing Sheets

(56) References Cited

U.S. PATENT DOCUMENTS

| | | | |
|---|---|---|---|
| 8,236,535 B2* | 8/2012 | Medoff et al. | 435/162 |
| 8,852,901 B2* | 10/2014 | Medoff et al. | 435/134 |
| 2006/0154353 A1 | 7/2006 | Duan et al. | |
| 2009/0117635 A1* | 5/2009 | Bradley et al. | 435/165 |
| 2010/0124583 A1 | 5/2010 | Medoff | |

OTHER PUBLICATIONS

Parish et al., Aug. 2009, Understanding the Ruminant Animal's Digestive System, The Cattle Site, available online at: www.thecattlesite.com/articles/2095/understanding-the-ruminant-animals-digestive-system.*

Oleskowicz-Popiel et al., 2007; IDS; Ethanol production from maize silage as lignocellulosic biomass in anaerobically digested and wet-oxidized manure, Biosource Technology, 99: 5327-5334.*

French, 2006; Kernel Processing—Getting more out of corn silage, Dairy Science Dept., VA Tech, accessed online at www2.dasc.vt.edu/extension/nutritioncc/frnch99a.pdf.*

Wallace et al., Feasibility Study for Co-Locating and Integrating Ethanol Production Plants from Corn Starch and Lignocellulosic Feedstocks, A Joint Study Sponsored by the U.S. Dept. of Agriculture and the U.S. Dept. of Energy, Jan. 2005, Available online at: www.nrel.gov/docs/fy05osti/37092.pdf.*

Bates et al., "Growing and Harvesting Switchgrass for Ethanol Production in Tennessee", University of Tennessee Institute of Agriculture: Accessed Dec. 17, 2012, online at: forages.tennessee.edu/Page18-%20Switchgrass%20for%20Forage/SP701-B.pdf.

A.B. Thomsen et al., "Manure Based Bioethanol and Biogas Co-Production", Baltic BioRefinery Symposium, May 26-28, 2005, Aalborg University Esbjerg Denmark, Proceedings, "published" before Jun. 11, 2005, pp. 41-52, XP002659398.

M.W. Lau et al., "Ethanolic Fermentation of Hydrolysates from Ammonia Fiber Expansion (AFEX) Treated Corn Stover and Distillers Grain Without Detoxification and External Nutrient Supplementation," Biotechnology and Bioengineering, Feb. 15, 2008, vol. 99, No. 3, pp. 529-539, XP002659400.

M.H. Thomsen, "Complex Media from Processing of Agricultural Crops for Microbial Fermentation," Applied Microbiology and Biotechnology, Springer, Berlin, DE, vol. 68, No. 5, Sep. 1, 2005, pp. 598-606, XP019331963.

Bi Dexi et al., "Utilization of Dry Distiller's Grain and Solubles as Nutrient Supplement in the Simultaneous Saccharification and Ethanol Fermentation at High Solids Loading of Corn Stover", Biotechnology Letters, vol. 33, No. 2, Feb. 2011, pp. 273-276, XP000002659401.

ISR for corresponding application PCT/US2011/044271, mailed Oct. 25, 2011, 5 pages.

Written Opinion for corresponding application PCT/US2011/044271, mailed Oct. 25, 2011, 7 pages.

Madsen, M., Lomborg, C. J., Holm-Nielsen, J. B., Esbensen, K., & Karlsen, E. (Eds.) Baltic Biorefinery Symposium. Esbjerg: Aalborg Universitet. 178 pages (2005).

* cited by examiner

PROCESSING BIOMASS

RELATED APPLICATIONS

This application is a continuation application of U.S. patent application Ser. No. 13/184,138, filed Jul. 15, 2011, which claims priority to U.S. Provisional Application Ser. No. 61/365,493, filed Jul. 19, 2010. The complete disclosure of these applications is hereby incorporated by reference herein.

BACKGROUND

Cellulosic and lignocellulosic materials are produced, processed, and used in large quantities in a number of applications. Often such materials are used once, and then discarded as waste, or are simply considered to be waste materials, e.g., sewage, bagasse, sawdust, and stover.

Various cellulosic and lignocellulosic materials, their uses, and applications have been described in U.S. Pat. Nos. 7,074,918, 6,448,307, 6,258,876, 6,207,729, 5,973,035 and 5,952,105; and in various patent applications, including "FIBROUS MATERIALS AND COMPOSITES", PCT/US2006/010648, filed on Mar. 23, 2006, AND "FIBROUS MATERIALS AND COMPOSITES", U.S. Patent Application Publication No. 2007/0045456.

SUMMARY

Generally, this invention relates to bioprocessing of carbon-containing materials, such as carbohydrate-containing materials (e.g., biomass materials, biomass-derived materials or chitin), in particular cellulosic and lignocellulosic materials, and saccharified carbohydrate-containing materials. The bioprocessing techniques disclosed herein include combining the carbohydrate-containing materials with a microorganism that utilizes the carbohydrate-containing material, or its saccharified derivative, to produce a product or intermediate. This process is generally performed in a fluid medium, and in some implementations comprises fermentation.

A typical biomass resource contains cellulose, hemicellulose, and lignin plus lesser amounts of proteins, extractables and minerals. The complex carbohydrates contained in the cellulose and hemicellulose fractions can be processed into fermentable sugars, which can then be converted by bioprocessing into a variety of products, such as alcohols or organic acids. The product obtained depends upon the microorganism utilized and the conditions under which the bioprocessing occurs.

Unlike traditional fermentation feedstocks such as corn, grapes, and the like, cellulosic and lignocellulosic materials generally contain relatively low to negligible levels of nutrients. This is particularly true of feedstocks that have been processed, e.g., by pulping, for example waste paper and waste paper pulp. As a result, when such feedstocks are used fermentation generally proceeds slowly (if at all), and it can be difficult to obtain high concentrations of ethanol. While commercially available nutrient packages, such as peptone or yeast nitrogen base, can be added to the fermentation medium, such materials are generally expensive, impacting the economic viability of large-scale fermentation processes.

The inventors have found that by adding particular nutrients to the bioprocessing medium to feed the microorganisms, the efficiency of the bioprocess can be significantly enhanced and the cost can be significantly reduced. The nutrients include a food product, e.g., a grain or vegetable; a residue of a food product, e.g., a residue of a crop product such as rice bran, or a residue of a meat product, e.g., stock, renderings, bouillon or extract of beef, chicken, pork or the like; or mixtures thereof. These will be referred to collectively herein as "food-based nutrient sources." Because food-based nutrient sources are used, nutrients can be supplied to the fermentation process at relatively low cost, reducing the overall cost of a product produced by the process. The food-based nutrient source can be low in sugar content, since the material is being used primarily or solely as a nutrient source, rather than as a fermentation feedstock. Thus, materials can be used that are not valued as a sugar source.

In some implementations, the food-based nutrient source is delivered as part of a nutrient package, which may include one or more additional ingredients. In some preferred implementations, the nutrient package further includes a nitrogen source, e.g., urea, ammonia, ammonium sulfate, and mixtures thereof.

In one aspect, the invention features a method that includes combining a feedstock, comprising a carbon-containing material, such as a cellulosic or lignocellulosic material and/or a saccharified cellulosic or lignocellulosic material, with a microorganism and a food-based nutrient source to form a mixture, the microorganism utilizing the feedstock to produce a product or intermediate.

Some implementations include one or more of the following features. In some cases, the food-based nutrient source is selected from the group consisting of grains, vegetables, residues of grains, residues of vegetables, residues of meat (e.g., stock, extract, bouillon or renderings), and mixtures thereof. For example, the nutrient source may be selected from the group consisting of wheat, oats, barley, soybeans, peas, legumes, potatoes, corn, rice bran, corn meal, wheat bran, meat product residues, and mixtures thereof.

The product can be or include, for example, a fuel selected from the group consisting of hydrogen, alcohols, organic acids, hydrocarbons, and mixtures thereof. For example, the product may comprise an alcohol selected from the group consisting of methanol, ethanol, propanol, isopropanol, n-butanol, ethylene glycol, propylene glycol, 1,4-butane diol, glycerin, and mixtures thereof. In some cases, the product may be an organic acid selected from the group consisting of formic acid, acetic acid, propionic acid, butyric acid, valeric acid, caproic, palmitic acid, stearic acid, oxalic acid, malonic acid, succinic acid, glutaric acid, oleic acid, linoleic acid, glycolic acid, lactic acid, γ-hydroxybutyric acid and mixtures thereof. Hydrocarbons include, for example, methane, ethane, propane, isobutene, pentane, n-hexane, and mixtures thereof. Other products and intermediates may also be produced.

The utilizing step can include, for example, saccharification and/or fermentation. In some cases, the utilizing step includes simultaneous saccharification and fermentation (SSF). The microorganism may include, for example, a yeast and/or an enzyme, such as any of those described in detail herein. In some cases, saccharification may be conducted at a pH of about 3.8 to 4.2 and fermentation may be conducted at a pH of about 4.8 to 5.2, and the method may further include adjusting the pH between saccharification and fermentation. The mixture may, in some cases, include a nitrogen source, which may be part of a nutrient package or may be added separately. The nitrogen source may be, for example, selected from the group consisting of urea, ammonia, ammonium sulfate, and mixtures thereof.

In some preferred implementations, the mixture further comprises an enzyme system selected to release nutrients, e.g., nitrogen, amino acids, and fats, from the food-based nutrient source. For example, the enzyme system may include one or more enzymes selected from the group consisting of amylases, proteases, and mixtures thereof. In some cases, the enzyme system comprises a protease and an amylase.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Using the methods and nutrient packages described herein, carbon-containing materials such as cellulosic and lignocellulosic materials and their saccharified derivatives can be bioprocessed, e.g., using fermentation, to produce useful intermediates and products such as those described herein.

The inventors have found that by adding low levels of a food product and/or a food residue to the fermentation batch, efficient fermentation can be obtained, resulting in relatively high concentrations of ethanol, e.g., up to 10%, 15%, 20%, 25%, or even up to 30% or more. In some cases, concentrations can be, for example, from about 0.1 to 80 g/L, e.g., from about 0.1 to 40 g/L, about 0.5 to 20 g/L, about 1 to 10 g/L or in some implementations from about 1 to 5 g/L. The concentration used will vary depending on the nutrient profile of the material(s) used.

Suitable food-based nutrient sources include grains, e.g., wheat, oats, and barley, and vegetables, e.g., soybeans, peas, legumes, potatoes, and corn, and residues of such materials, e.g., rice bran, corn meal, and wheat bran. These represent but a few examples of the many grains and vegetables that may be used. As discussed above, in addition or alternatively the food-based nutrient source may include meat residues such as the stock, bouillon, extract or renderings of beef, chicken, pork, or other meats. The food-based nutrient source may include mixtures of two or more grains and/or vegetables and/or meat residues. Advantageously, such materials are generally low cost. In some cases, materials are used that are otherwise considered waste, e.g., food products or residues that would otherwise have to be landfilled.

In addition to the food-based nutrient source, preferred nutrient packages contain a nitrogen source. Suitable nitrogen sources include, for example, urea, ammonia, ammonium sulfate, and mixtures thereof. In some implementations, the nitrogen source is added in a concentration of about 1-10, 2-8 or preferably 3-6 g/L based on the volume of the liquid medium.

Other compounds that may be included in the nutrient package include phosphates, which are used by the microorganism for replication.

In preferred implementations, the nutrient package is used with a particular combination of enzymes that includes one or more enzymes selected to saccharify on the cellulosic or lignocellulosic material, and one or more enzymes selected to release nutrients (e.g., nitrogen, amino acids and fats) from the food-based nutrient source. In some cases, the combination of enzymes includes an amylase, to break down starch in the nutrient source, and a protease, to hydrolyze protein and produce peptides from the nutrient source. Preferred enzyme combinations will be discussed in detail below.

Processes in which the food-based nutrient sources or nutrient packages may be used will now be discussed.

Converting Cellulosic and Lignocellulosic Materials to Alcohols

Figure 1:
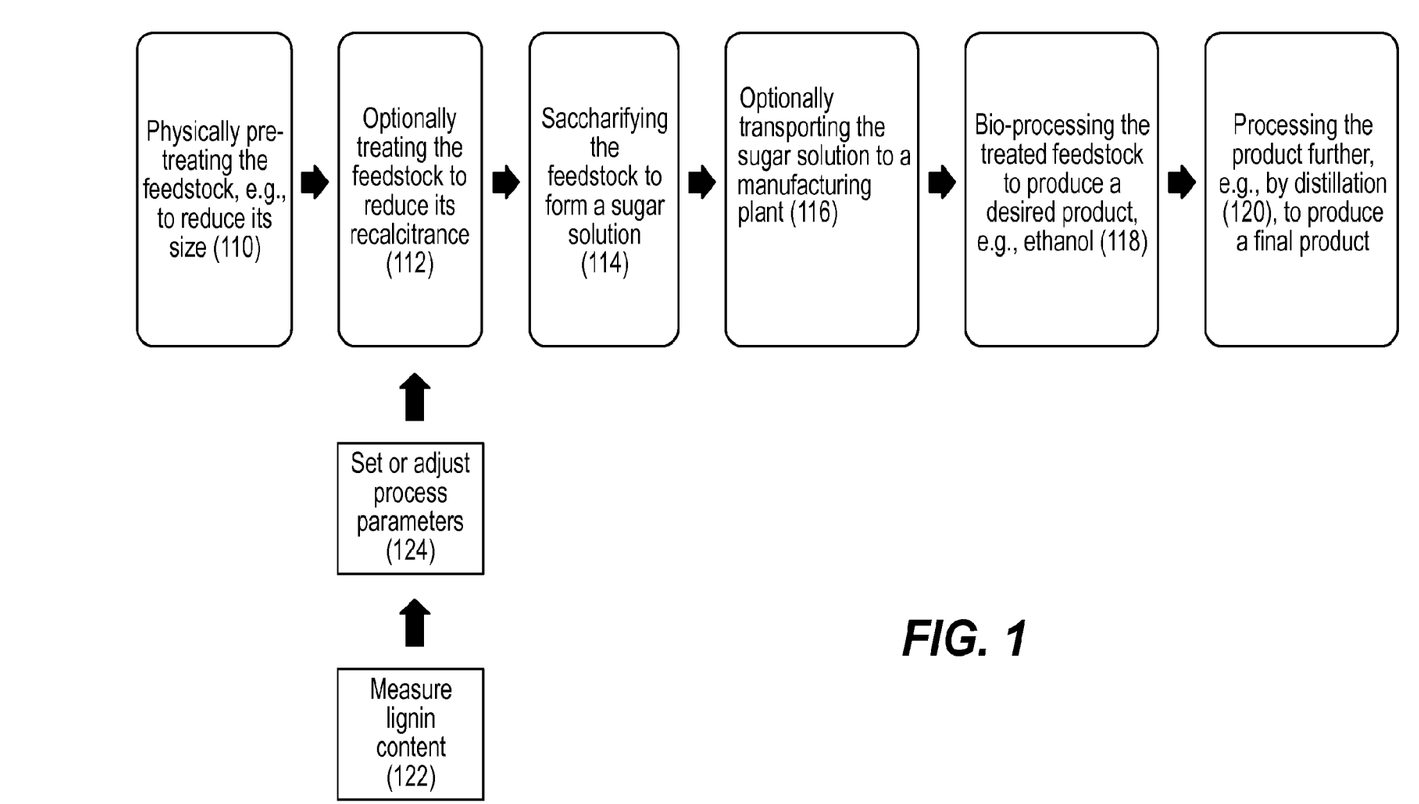
FIG. 1 is a flow diagram illustrating conversion of a feedstock to ethanol via production of a glucose solution.

Referring to FIG. 1, a process for manufacturing an alcohol, e.g., ethanol, can include, for example, optionally mechanically treating the feedstock (step 110), before and/or after this treatment, optionally treating the feedstock with another physical treatment, for example irradiation (e.g., electron beam irradiation), to further reduce its recalcitrance (step 112), saccharifying the feedstock to form a sugar solution (step 114), optionally transporting, e.g., by pipeline, railcar, truck or barge, the solution (or the feedstock, enzyme and water, if saccharification is performed en route) to a manufacturing plant (step 116), and then bio-processing the treated feedstock to produce a desired product (step 118), which is then processed further, e.g., by distillation (step 120). If desired, lignin content can be measured (step 122) and process parameters can be set or adjusted based on this measurement (step 124), as described in U.S. Provisional Application No. 61/151,724, filed on Feb. 11, 2009, the complete disclosure of which is incorporated herein by reference.

The food-based nutrient source or nutrient package is present during bio-processing (step 118), e.g., fermentation, and may in some preferred implementations also be present during the saccharification step (step 114). In some implementations, the food-based nutrient source or nutrient package is added at the beginning of step 114, along with an enzyme combination suitable for saccharification, fermentation, and release of nutrients from the food-based nutrient source. Saccharification is conducted under a first set of process conditions (e.g., temperature and pH), and then when saccharification has proceeded to a desired extent the process conditions are adjusted (e.g., by adjusting pH from 4 to 5) to allow fermentation to proceed.

Figure 2:
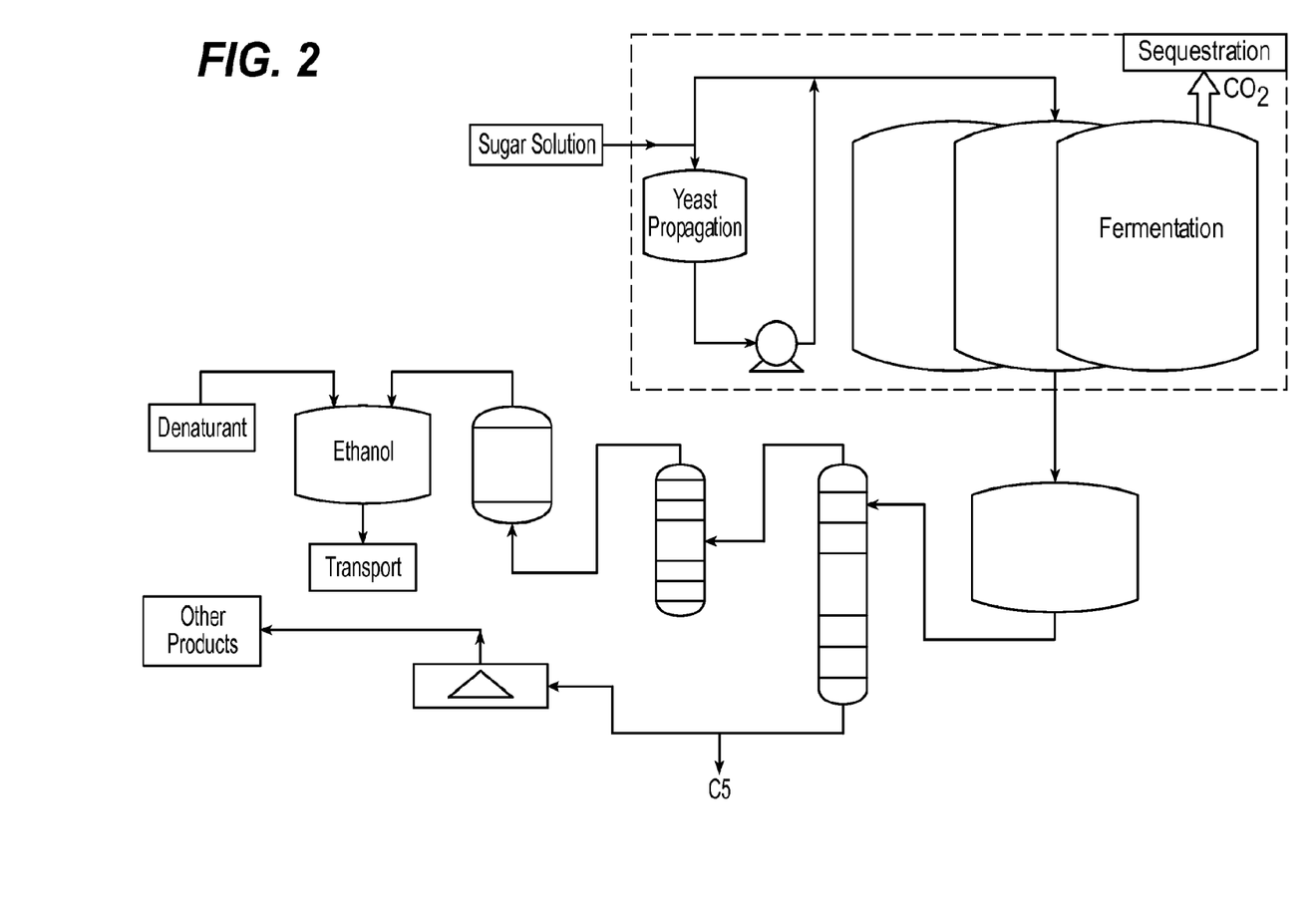
FIG. 2 is a schematic diagram of an ethanol manufacturing facility.

The manufacturing plant used in steps 118-120 (and in some cases all of the steps described above) can be, for example, an existing starch-based or sugar-based ethanol plant or one that has been retrofitted by removing or decommissioning the equipment upstream from the bio-processing system (which in a typical ethanol plant generally includes grain receiving equipment, a hammermill, a slurry mixer, cooking equipment and liquefaction equipment). In some cases, the feedstock received by the plant can be input directly into the fermentation equipment. A retrofitted plant is shown schematically in FIG. 2.

Steps 110-112 are described, for example, in U.S. Ser. No. 12/429,045, filed Apr. 23, 2009, the complete disclosure of which is incorporated herein by reference. Steps 114, 118 and 120 (saccharification, fermentation, and distillation), which pertain to the production of alcohol by bioprocessing, will now be discussed further.

Saccharification

In order to convert the feedstock to fermentable sugars, the cellulose in the feedstock is hydrolyzed by a saccharifying agent, e.g., an enzyme, a process referred to as saccharification. The materials that include the cellulose are treated with the enzyme, e.g., by combining the material and the enzyme in a solvent, e.g., in an aqueous solution.

Figure 3:
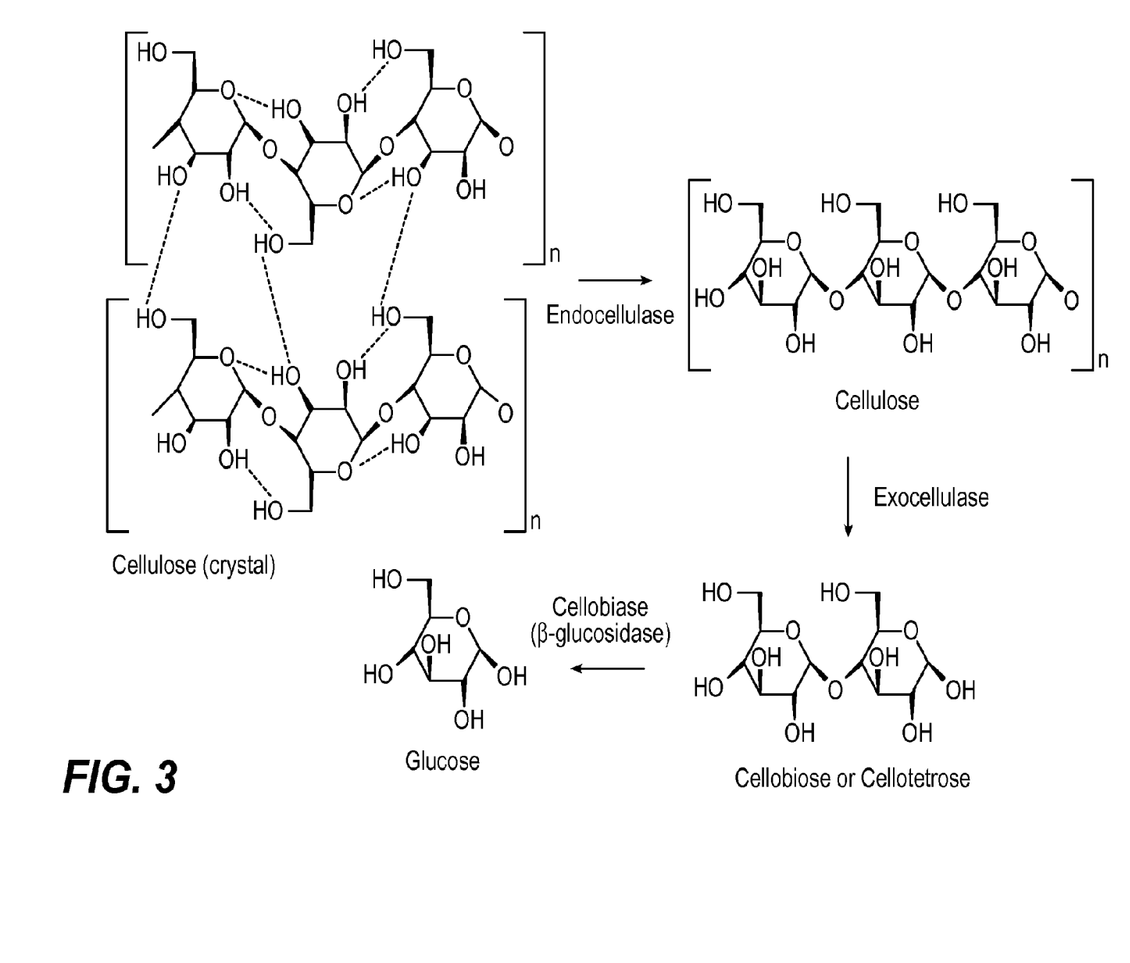
FIG. 3 is a diagram illustrating the enzymatic hydrolysis of cellulose to glucose.

Enzymes and biomass-destroying organisms that break down biomass, such as the cellulose and/or the lignin portions of the biomass, contain or manufacture various cellulolytic enzymes (cellulases), ligninases or various small molecule biomass-destroying metabolites. These enzymes may be a complex of enzymes that act synergistically to degrade crystalline cellulose or the lignin portions of biomass. Examples of cellulolytic enzymes include: endoglucanases, cellobiohydrolases, and cellobiases (β-glucosidases). Referring to FIG. 3, a cellulosic substrate is initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble 1,4-linked dimer of glucose. Finally cellobiase cleaves cellobiose to yield glucose.

Suitable saccharifying agents are described, for example, in the Materials section below.

As noted above, the food-based nutrient source or nutrient package is preferably added prior to or during saccharification, and an enzyme is added that is selected to release nutrients from the food-based nutrient source. Suitable enzymes are described, for example, in the Materials section below.

The saccharification process can be partially or completely performed in a tank (e.g., a tank having a volume of at least 4000, 40,000, 400,000, or 1,000,000 L) in a manufacturing plant, and/or can be partially or completely performed in transit, e.g., in a rail car, tanker truck, or in a supertanker or the hold of a ship. The time required for complete saccharification will depend on the process conditions and the feedstock and enzyme used. If saccharification is performed in a manufacturing plant under controlled conditions, the cellulose may be substantially entirely converted to glucose in about 12-96 hours. If saccharification is performed partially or completely in transit, saccharification may take longer.

It is generally preferred that the tank contents be mixed during saccharification, e.g., using jet mixing as described in U.S. Provisional Application No. 61/218,832, the full disclosure of which is incorporated by reference herein.

The addition of surfactants can enhance the rate of saccharification. Examples of surfactants include non-ionic surfactants, such as a Tween® 20 or Tween® 80 polyethylene glycol surfactants, ionic surfactants, or amphoteric surfactants.

It is generally preferred that the concentration of the resulting glucose solution be relatively high, e.g., greater than 40%, or greater than 50, 60, 70, 80, 90 or even greater than 95% by weight. This reduces the volume to be shipped, if saccharification and fermentation are performed at different locations, and also inhibits microbial growth in the solution. However, lower concentrations may be used, in which case it may be desirable to add an antimicrobial additive, e.g., a broad spectrum antibiotic, in a low concentration, e.g., 50 to 150 ppm. Other suitable antibiotics include amphotericin B, ampicillin, chloramphenicol, ciprofloxacin, gentamicin, hygromycin B, kanamycin, neomycin, penicillin, puromycin, streptomycin. Antibiotics will inhibit growth of microorganisms during transport and storage, and can be used at appropriate concentrations, e.g., between 15 and 1000 ppm by weight, e.g., between 25 and 500 ppm, or between 50 and 150 ppm. If desired, an antibiotic can be included even if the sugar concentration is relatively high.

A relatively high concentration solution can be obtained by limiting the amount of water added to the feedstock with the enzyme. The concentration can be controlled, e.g., by controlling how much saccharification takes place. For example, concentration can be increased by adding more feedstock to the solution. In order to keep the sugar that is being produced in solution, a surfactant can be added, e.g., one of those discussed above. Solubility can also be increased by increasing the temperature of the solution. For example, the solution can be maintained at a temperature of 40-50° C., 60-80° C., or even higher.

In some embodiments, the feedstock is processed to convert it to a convenient and concentrated solid material, e.g., in a powdered, granulate or particulate form. The concentrated material can be in a purified, or a raw or crude form. The concentrated form can have, for example, a total sugar concentration of between about 90 percent by weight and about 100 percent by weight, e.g., 92, 94, 96 or 98 percent by weight sugar. Such a form can be particularly cost effective to ship, e.g., to a bioprocessing facility, such as a biofuel manufacturing plant. Such a form can also be advantageous to store and handle, easier to manufacture and becomes both an intermediate and a product, providing an option to the biorefinery as to which products to manufacture.

In some instances, the powdered, granulate or particulate material can also include one or more of the materials, e.g., additives or chemicals, described herein, such as the food-based nutrient or nutrient package, a nitrogen source, e.g., urea, a surfactant, an enzyme, or any microorganism described herein. In some instances, all materials needed for a bio-process are combined in the powdered, granulate or particulate material. Such a form can be a particularly convenient form for transporting to a remote bioprocessing facility, such as a remote biofuels manufacturing facility. Such a form can also be advantageous to store and handle.

In some instances, the powdered, granulate or particulate material (with or without added materials, such as additives and chemicals) can be treated by any of the physical treatments described in U.S. Ser. No. 12/429,045, incorporated by reference above. For example, irradiating the powdered, granulate or particulate material can increase its solubility and can sterilize the material so that a bioprocessing facility can integrate the material into their process directly as may be required for a contemplated intermediate or product.

In certain instances, the powdered, granulate or particulate material (with or without added materials, such as additives and chemicals) can be carried in a structure or a carrier for ease of transport, storage or handling. For example, the structure or carrier can include or incorporate a bag or liner, such as a degradable bag or liner. Such a form can be particularly useful for adding directly to a bioprocess system.

Fermentation

Microorganisms can produce a number of useful intermediates and products by fermenting a low molecular weight sugar produced by saccharifying the treated biomass materials. For example, fermentation or other bioprocesses can produce alcohols, organic acids, hydrocarbons, hydrogen, proteins or mixtures of any of these materials.

Yeast and *Zymomonas* bacteria, for example, can be used for fermentation or conversion. Other microorganisms are discussed in the Materials section, below. The optimum pH for yeast is from about pH 4 to 5, while the optimum pH for *Zymomonas* is from about pH 5 to 6. Typical fermentation times are about 24 to 96 hours with temperatures in the range of 26° C. to 40° C., however thermophilic microorganisms prefer higher temperatures.

In some embodiments, all or a portion of the fermentation process can be interrupted before the low molecular weight sugar is completely converted to ethanol. The intermediate fermentation products include high concentrations of sugar and carbohydrates. These intermediate fermentation products can be used in preparation of food for human or animal consumption. Additionally or alternatively, the intermediate fermentation products can be ground to a fine particle size in a stainless-steel laboratory mill to produce a flour-like substance.

Mobile fermentors can be utilized, as described in U.S. Provisional Patent Application Ser. 60/832,735, now Published International Application No. WO 2008/011598. Similarly, the saccharification equipment can be mobile. Further, saccharification and/or fermentation may be performed in part or entirely during transit.

Distillation

After fermentation, the resulting fluids can be distilled using, for example, a "beer column" to separate ethanol and other alcohols from the majority of water and residual solids. The vapor exiting the beer column can be, e.g., 35% by weight ethanol and can be fed to a rectification column. A mixture of nearly azeotropic (92.5%) ethanol and water from the rectification column can be purified to pure (99.5%) ethanol using vapor-phase molecular sieves. The beer column bottoms can be sent to the first effect of a three-effect evaporator. The rectification column reflux condenser can provide heat for this first effect. After the first effect, solids can be separated using a centrifuge and dried in a rotary dryer. A portion (25%) of the centrifuge effluent can be recycled to fermentation and the rest sent to the second and third evaporator effects. Most of the evaporator condensate can be returned to the process as fairly clean condensate with a small portion split off to waste water treatment to prevent build-up of low-boiling compounds.

Intermediates and Products

The processes and nutrients discussed herein can be used to convert carbohydrate-containing materials, e.g., cellulosic or lignocellulosic materials, to one or more products, such as energy, fuels, foods and materials. Specific examples of products include, but are not limited to, hydrogen, alcohols (e.g., monohydric alcohols or dihydric alcohols, such as ethanol, n-propanol or n-butanol), hydrated or hydrous alcohols, e.g., containing greater than 10%, 20%, 30% or even greater than 40% water, sugars, biodiesel, organic acids (e.g., acetic acid and/or lactic acid), hydrocarbons, co-products (e.g., proteins, such as cellulolytic proteins (enzymes) or single cell proteins), and mixtures of any of these in any combination or relative concentration, and optionally in combination with any additives, e.g., fuel additives. Other examples include carboxylic acids, such as acetic acid or butyric acid, salts of a carboxylic acid, a mixture of carboxylic acids and salts of carboxylic acids and esters of carboxylic acids (e.g., methyl, ethyl and n-propyl esters), ketones, aldehydes, alpha, beta unsaturated acids, such as acrylic acid and olefins, such as ethylene. Other alcohols and alcohol derivatives include propanol, propylene glycol, 1,4-butanediol, 1,3-propanediol, methyl or ethyl esters of any of these alcohols. Other products include methyl acrylate, methylmethacrylate, lactic acid, propionic acid, butyric acid, succinic acid, 3-hydroxypropionic acid, a salt of any of the acids and a mixture of any of the acids and respective salts.

Other intermediates and products, including food and pharmaceutical products, are described in U.S. Ser. No. 12/417,900, the full disclosure of which is hereby incorporated by reference herein.

Materials

Nutrient Package Ingredients

As discussed above, preferred nutrient packages contain a food-based nutrient source, a nitrogen source, and in some cases other ingredients, e.g., phosphates. Suitable food-based nutrient sources include grains and vegetables, including those discussed above and many others. The food-based nutrient source may include mixtures of two or more grains and/or vegetables.

Preferred nutrient packages may include about 2 to 5% by volume weight of a food-based nutrient source, e.g., 3-4% by volume weight of rice bran meal or 4-5% by volume weight of corn meal, about 3 to 4 g/L of a nitrogen source, e.g., about 3.5 g/L urea, and about 8 to 12 g/L of a non-ionic surfactant, e.g., about 10 g/L Tween® 80 surfactant.

Enzymes for Releasing Nutrients

As discussed above, it is preferred that the saccharification and/or fermentation mixture further include an enzyme system selected to release nutrients, e.g., nitrogen, amino acids, and fats, from the food-based nutrient source. For example, the enzyme system may include one or more enzymes selected from the group consisting of amylases, proteases, and mixtures thereof.

In some cases, the enzyme system comprises a protease and an amylase. An example of a suitable protease is FERMGEN™ acid proteolytic enzyme, commercially available from Genencor®, a division of Danisco. This enzyme is a fungal protease composed of 5-10% Aspergillopepsin 1 in an aqueous solution with glycerol, sodium sulfate, and sodium benzoate. An example of a suitable amylase is STARGEN™ enzyme, commercially available from Genencor®, a division of Danisco. This enzyme is a glucoamylase and alpha-amylase blend, containing *Aspergillus kawachi* alpha-amylase expressed in *Trichoderma reesei* and a gluco-amylase from *Trichoderma reesei*.

In some preferred implementations, the amylase and protease are each included at a concentration of about 0.5 to 1.5% by weight based on the weight of the food-based nutrient source added, e.g., about 1% by weight each. These are very low concentrations, compared to the concentrations that are generally required when the same food-based materials are being used as a feedstock for saccharification and fermentation, rather than as a nutrient source. For example, recommended concentrations of FERMGEN™ enzyme and STARGEN™ enzyme are 26-38% w/w and 20-34% w/w, respectively, when those enzymes are used in the saccharification and fermentation of corn and grains to ethanol.

While it is preferred that a combination of protease and amylase be used, in some cases one or the other may be used alone, and/or other enzymes may be used that are capable of releasing nutrients from the food-based nutrient source.

Biomass Materials

The biomass can be, e.g., a cellulosic or lignocellulosic material. Such materials include paper and paper products (e.g., polycoated paper and Kraft paper), wood, wood-related materials, e.g., particle board, grasses, rice hulls, bagasse, jute, hemp, flax, bamboo, sisal, abaca, straw, switchgrass, alfalfa, hay, corn cobs, corn stover, coconut hair; and materials high in α-cellulose content, e.g., cotton. Feedstocks can be obtained from virgin scrap textile materials, e.g., remnants, post consumer waste, e.g., rags. When paper products are used they can be virgin materials, e.g., scrap virgin materials, or they can be post-consumer waste. Aside from virgin raw materials, post-consumer, industrial (e.g., offal), and processing waste (e.g., effluent from paper processing) can also be used as fiber sources. Biomass feedstocks can also be obtained or derived from human (e.g., sewage), animal or plant wastes. Additional cellulosic and lignocellulosic materials have been described in U.S. Pat. Nos. 6,448,307, 6,258,876, 6,207,729, 5,973,035 and 5,952,105.

In some embodiments, the biomass material includes a carbohydrate that is or includes a material having one or more β-1,4-linkages and having a number average molecular weight between about 3,000 and 50,000. Such a carbohydrate is or includes cellulose, which is derived from (β-glucose) through condensation of β(1,4)-glycosidic bonds. This linkage contrasts itself with that for α(1,4)-glycosidic bonds present in starch and other carbohydrates.

Saccharifying Agents

Suitable enzymes include cellobiases and cellulases capable of degrading biomass.

Suitable cellobiases include a cellobiase from *Aspergillus niger* sold under the tradename NOVOZYME 188™.

Cellulases are capable of degrading biomass, and may be of fungal or bacterial origin. Suitable enzymes include cellulases from the genera *Bacillus, Pseudomonas, Humicola, Fusarium, Thielavia, Acremonium, Chrysosporium* and *Trichoderma*, and include species of *Humicola, Coprinus, Thielavia, Fusarium, Myceliophthora, Acremonium, Cephalosporium, Scytalidium, Penicillium* or *Aspergillus* (see, e.g., EP 458162), especially those produced by a strain selected from the species *Humicola insolens* (reclassified as *Scytalidium thermophilum*, see, e.g., U.S. Pat. No. 4,435,307), *Coprinus cinereus, Fusarium oxysporum, Myceliophthora thermophila, Meripilus giganteus, Thielavia terrestris, Acremonium* sp., *Acremonium persicinum, Acremonium acremonium, Acremonium brachypenium, Acremonium dichromosporum, Acremonium obclavatum, Acremonium pinkertoniae, Acremonium roseogriseum, Acremonium incoloratum*, and *Acremonium furatum*; preferably from the species *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic enzymes may also be obtained from *Chrysosporium*, preferably a strain of *Chrysosporium lucknowense*. Additionally, *Trichoderma* (particularly *Trichoderma viride, Trichoderma reesei*, and *Trichoderma koningii*), alkalophilic *Bacillus* (see, for example, U.S. Pat. No. 3,844,890 and EP 458162), and *Streptomyces* (see, e.g., EP 458162) may be used.

Enzyme complexes may be utilized, such as those available from Genencor® under the tradename ACCELLERASE®, for example, Accellerase® 1500 enzyme complex. Accellerase® 1500 enzyme complex contains multiple enzyme activities, mainly exoglucanase, endoglucanase (2200-2800 CMC U/g), hemi-cellulase, and beta-glucosidase (525-775 pNPG U/g), and has a pH of 4.6 to 5.0. The endoglucanase activity of the enzyme complex is expressed in carboxymethylcellulose activity units (CMC U), while the beta-glucosidase activity is reported in pNP-glucoside activity units (pNPG U). Another suitable enzyme complex is Accellerase® Duet enzyme complex. Accellerase® Duet enzyme complex also contains multiple enzyme activities, mainly exoglucanase, endoglucanase (2400-3000 CMC U/g), hemi-cellulase (including xylanase, >3600 ABX U/g), and beta-glucosidase (>400 pNPG U/g), and has a pH of 4.3 to 4.6. The endoglucanase activity of the enzyme complex is expressed in carboxymethylcellulose activity units (CMC U), while the beta-glucosidase activity is reported in pNP-glucoside activity units (pNPG U) and Xylanase activity is reported in Acid Birchwood Xylanase Units (ABXU). In some embodiments, a blend of Accellerase® 1500 or Accellerase® Duet enzyme complex with NOVOZYME™ 188 cellobiase is used.

Fermentation Agents

The microorganism(s) used in fermentation can be natural microorganisms and/or engineered microorganisms. For example, the microorganism can be a bacterium, e.g., a cellulolytic bacterium, a fungus, e.g., a yeast, a plant or a protist, e.g., an algae, a protozoa or a fungus-like protist, e.g., a slime mold. When the organisms are compatible, mixtures of organisms can be utilized.

Suitable fermenting microorganisms have the ability to convert carbohydrates, such as glucose, xylose, arabinose, mannose, galactose, oligosaccharides or polysaccharides into fermentation products. Fermenting microorganisms include strains of the genus *Sacchromyces* spp. e.g., *Sacchromyces cerevisiae* (baker's yeast), *Saccharomyces distaticus, Saccharomyces uvarum*; the genus *Kluyveromyces*, e.g., species *Kluyveromyces marxianus, Kluyveromyces fragilis*; the genus *Candida*, e.g., *Candida pseudotropicalis*, and *Candida brassicae, Pichia stipitis* (a relative of *Candida shehatae*, the genus *Clavispora*, e.g., species *Clavispora lusitaniae* and *Clavispora opuntiae*, the genus *Pachysolen*, e.g., species *Pachysolen tannophilus*, the genus *Bretannomyces*, e.g., species *Bretannomyces clausenii* (Philippidis, G. P., 1996, Cellulose bioconversion technology, in Handbook on Bioethanol: Production and Utilization, Wyman, C. E., ed., Taylor & Francis, Washington, D.C., 179-212).

Commercially available yeasts include, for example, Red Star®/Lesaffre Ethanol Red (available from Red Star/Lesaffre, USA), FALI® (available from Fleischmann's Yeast, a division of Burns Philip Food Inc., USA), SUPERSTART® (available from Alltech, now Lalemand), GERT STRAND® (available from Gert Strand AB, Sweden) and FERMOL® (available from DSM Specialties).

Bacteria may also be used in fermentation, e.g., *Zymomonas mobilis* and *Clostridium thermocellum* (Philippidis, 1996, supra).

EXAMPLE 1

A feedstock (referred to in Example 2 as "XP") was produced using the following procedure.

A 1500 pound skid of virgin bleached white Kraft board having a bulk density of 30 lb/ft$^3$ was obtained from International Paper. The material was cut into pieces 8¼ inches by 11 inches using a guillotine cutter and fed to a Munson rotary knife cutter, Model SC30. The discharge screen had ⅛ inch openings. The gap between the rotary and fixed blades was set to approximately 0.020 inch. The rotary knife cutter sheared the cut pieces, releasing a fibrous material.

EXAMPLE 2

A medium was prepared by heating 4 L deionized water to 50° C. and mixing while adding 4% by volume weight rice bran meal, 3.405 g/L Urea, and 10 g/L Tween 80® surfactant. Next, three enzymes were added, in the following amounts:

ACCELLERASE® enzyme 0.25 mL/1 gram XP feedstock
STARGEN™ enzyme 1% by bran weight
FERMGEN™ enzyme 1% by bran weight The ACCELLERASE was added at 0 hours, and the other two enzymes were added at 3 hours.

The XP feedstock was then added in increments, the amount and frequency of which was determined by consistency of the mixture and the mixing speed. The material was added over a 27 hour period, in increments of increments of 150-275 grams. The total amount added was 1096 grams.

Temperature fluctuations were monitored during mixing, to prevent heating over 55° C., which will tend to denature the enzymes.

Throughout the process, mixing was performed at 250 rpm, using an IKA ROTOTRON® mixer. The temperature was maintained at approximately 50° C., and the pH was about 3.7.

After the last increment of feedstock was added, at 27 hours, the batch was allowed to continue to saccharify to a total of 70 hours from the beginning of the process. At this point the glucose concentration was 90 g/L.

The saccharified mixture was transferred to a BioFlow® 115 bioreactor for fermentation. The parameters were then changed, and the mixture inoculated, to initiate fermentation. Mixing was performed with a Rushton impeller at 250 rpm, with air provided at 0.025 vvm, and the pH was adjusted to about 5.0. The temperature was reduced to about 30° C. pH control was provided using 1M $H_3PO_4$ (acid control) and 1M NaOH (base control). Inoculation was based on the following ratio: 1 mg of Superstart™ yeast to 1 g of glucose. The yeast was added directly to the mixture as a freeze dried inoculum.

After 20 hours of fermentation under these conditions, the concentration of ethanol in the mixture was about 50 g/L, and the concentration of glucose had dropped to about 0 g/L. This was only slightly lower than ethanol concentrations obtained by fermenting 150 g/L glucose and 40 g/L xylose in a medium containing 1.7 g/L YNB, 2.27 g/L Urea and 6.6 g/L soy peptones under the same processing conditions.

OTHER EMBODIMENTS

A number of embodiments of the invention have been described. Nevertheless, it will be understood that various modifications may be made without departing from the spirit and scope of the invention.

For example, while it is preferred for cost reasons that the nutrient packages disclosed herein include only food-based (and in particular vegetable and/or grain) nutrient sources, if desired the nutrient package can include mixtures of these nutrient sources with other non-food based or non-grain/non-vegetable food sources.

Accordingly, other embodiments are within the scope of the following claims.

What is claimed is:

1. A method for bioprocessing carbon-containing materials, the method comprising:
   providing within a bioreactor, a mixture comprising a carbon source, a microorganism, a nutrient package delivered separately from the carbon source comprising from 0.1 to 80 g/L of a food-based nutrient source, and an enzyme system comprising one or more enzymes selected to release nutrients from the food-based nutrient source; and
   maintaining the bioreactor under conditions effective for the microorganism to bioprocess the carbon source.

2. The method of claim 1 wherein the food-based nutrient source is selected from the group consisting of grains, vegetables, residues of grains, residues of vegetables, residues of meat products, and mixtures thereof.

3. The method of claim 1, further comprising separating a product from the mixture, wherein the product comprises a fuel selected from the group consisting of hydrogen, alcohols, organic acids, hydrocarbons, and mixtures thereof.

4. The method of claim 1, wherein said bioprocess comprises fermentation.

5. The method of claim 4 wherein the microorganism comprises a yeast.

6. The method of claim 4 wherein fermentation is conducted at a pH of about 4.8 to 5.2.

7. The method of claim 1, wherein said bioprocess comprises saccharification.

8. The method of claim 7, wherein the enzyme system further comprises one or more enzymes selected to saccharify carbon-containing materials.

9. The method of claim 8, wherein the one or more enzymes selected to saccharify carbon-containing materials comprises a hemicellulase or a cellulase.

10. The method of claim 7 wherein saccharification is conducted at a pH of about 3.8 to 4.2.

11. The method of claim 1 wherein the mixture further comprises a nitrogen source.

12. The method of claim 11 wherein the nitrogen source is selected from the group consisting of urea, ammonia, ammonium sulfate, and mixtures thereof.

13. The method of claim 2 wherein the food-based nutrient source is selected from the group consisting of wheat, oats, barley, soybeans, peas, legumes, potatoes, corn, rice bran, corn meal, wheat bran, and mixtures thereof.

14. The method of claim 1, wherein the enzyme system comprises one or more enzymes selected from the group consisting of amylases, proteases, and mixtures thereof.

15. The method of claim 1, wherein the enzyme system comprises a protease and an amylase.

16. The method of claim 15 wherein the enzyme system further comprises a hemicellulase or a cellulase.

17. The method of claim 1 wherein the mixture further comprises a medium.

18. The method of claim 17 wherein the concentration of the food-based nutrient source in the medium is from about 0.1 to 10 g/L.

19. The method of claim 3, wherein the alcohol is selected from the group consisting of methanol, ethanol, propanol, isopropanol, n-butanol, ethylene glycol, propylene glycol, 1,4-butane diol, glycerin, and mixtures thereof.

20. The method of claim 3, wherein the organic acid is selected from the group consisting of formic acid, acetic acid, propionic acid, butyric acid, valeric acid, caproic, palmitic acid, stearic acid, oxalic acid, malonic acid, succinic acid, glutaric acid, oleic acid, linoleic acid, glycolic acid, lactic acid, y-hydroxybutyric acid and mixtures thereof.

21. The method of claim 3, wherein the hydrocarbon is selected from the group consisting of methane, ethane, propane, isobutene, pentane, n-hexane, and mixtures thereof.

22. The method of claim 1, wherein the carbon-containing material has been treated to reduce its recalcitrance.

23. The method of claim 22, wherein the carbon-containing material has been treated with radiation.

24. The method of claim 23, wherein the radiation comprises an electron beam.

25. The method of claim 1, wherein the mixture further comprises a second carbon source, the nutrient package delivered separately from the second carbon source.

* * * * *